US006855821B2

(12) United States Patent
Du et al.

(10) Patent No.: US 6,855,821 B2
(45) Date of Patent: Feb. 15, 2005

(54) PROCESSES FOR PREPARING 1,3-DIOXOLANE NUCLEOSIDES

(75) Inventors: Jinfa Du, Lilburn, GA (US); Kyoichi A. Watanabe, Stone Mountain, GA (US)

(73) Assignee: Pharmasset, Ltd., Tucker, GA (US)

( * ) Notice: Subject to any disclaimer, the term of this patent is extended or adjusted under 35 U.S.C. 154(b) by 0 days.

(21) Appl. No.: 10/635,971

(22) Filed: Aug. 6, 2003

(65) Prior Publication Data

US 2004/0087806 A1 May 6, 2004

Related U.S. Application Data

(60) Provisional application No. 60/401,655, filed on Aug. 6, 2002.

(51) Int. Cl.$^7$ ............................................. C07D 473/00
(52) U.S. Cl. ........................ 544/265; 544/276; 544/277
(58) Field of Search ................................ 544/265, 276, 544/277

(56) References Cited

U.S. PATENT DOCUMENTS

| | | |
|---|---|---|
| 5,047,407 A | 9/1991 | Belleau et al. |
| 5,204,466 A | 4/1993 | Liotta et al. |
| 5,272,151 A | 12/1993 | Marzi et al. |
| 5,663,320 A | 9/1997 | Mansour et al. |
| 5,693,787 A | 12/1997 | Mansour et al. |
| 5,696,254 A | 12/1997 | Mansour et al. |
| 5,744,596 A | 4/1998 | Mansour et al. |
| 5,756,706 A | 5/1998 | Mansour et al. |
| 5,767,122 A | 6/1998 | Chu et al. |
| 5,792,773 A | 8/1998 | Chu et al. |
| 5,852,027 A | 12/1998 | Liotta et al. |
| 5,922,867 A | 7/1999 | Mansour et al. |
| 6,215,004 B1 | 4/2001 | Painter et al. |
| 6,358,963 B1 | 3/2002 | Nguyen-Ba |

OTHER PUBLICATIONS

Bauer, M., et al., "Iodide catalysis of oxidations with dimethyl sulfoxide: a convenient two–step synthesis of α–diketones from α–methylene ketones," *J. Org. Chem.*, 40(13):1990–1992 (1975).
Belleau, B., et al., "Design and activity of a novel class of nucleoside analogs effective against HIV–1," 5$^{th}$ *Int. Conf. on AIDS*, Montreal, Canada; Jun. 4–9, 1989; Abstr. No. T.C.O.I. and Poster No. 4576.
Choi, W.–B., et al., "In situ complexation directs the stereochemistry of N–glycosylation in the synthesis of oxathiolanyl and dioxolanyl nucleoside analogues," *J. Am. Chem. Soc.*, 113(24):9377–9379 (1991).
Chou, T.–S., et al., "A cyclization approach toward five–membered heteroaromatic o–quinodimethanes via fused–3–sulfolenes," *J. Chinese Chem. Soc.*, 44:299–307 (1997).

Corbet, A.H., et al., "DAPD," *Curr. Opin. Investig. Drugs*, 2(9):348–353 (2001).
Evans, C.A. et al., "Divergent asymmetric syntheses of dioxolane nucleoside analogues," *Tetrahedron: Asymmetry*, 4(11):2319–2322 (1993).
Grese, T. A., et al., "General approach to halogenated tetrahydrofuran natural products from red algae of the genus Laurencia. Total synthesis of (±)–kumausallene and (±)–1–epi–kumausallene," *J. Org. Chem.*, 58(9):2468–2477 (1993).
Gu, Z., et al., "Mechanism of action and in vitro activity of 1',3'–dioxolanylpurine nucleoside analogues against sensitive and drug–resistant human immunodeficiency virus type 1 variants," *Antimicrob. Agents Chemother.*, 43(10):2376–2382 (Oct. 1999).
Gu, Z., et al., "Anti–HIV–1 activities of 1,3–dioxolane guanine and 2,6–diaminopurine dioxolane," *Nucleosides Nucleotides*, 18(4&5):891–892 (1999).
Hambalek, R., et al., "A short synthesis of (±)–oxetanocin," *Tetrahedron Lett.*, 31(38):5445–5448 (1990).
Hanessian, S., et al., "Oxidation of alcohols with N–halosuccinimides—new and efficient variants," *Synthesis*, 1981:394–396 (May 1981).
Hann, R.H., et al., "The structures of the diacetone dulcitols," *J. Am. Chem. Soc.*, 61:2432–2442 (1939).
Haskins, W. T., et. al., "The isomeric 1,3– and 2,3–benzylidene–D–arabitols," *J. Am. Chem. Soc.*, 65(9):1663–1667 (Sep. 7, 1943).
Hopkins, M. H., et al., "Stereocontrolled preparation of tetrahydrofurans from acid–promoted rearrangements of allylic acetals," *J. Am. Chem. Soc.*, 113(14):5354–5365 (1991).
Kim, H.–O., et al., "L–β–(2S–4S)– and L–α–(2S,4R)–dioxolanyl nucleosides as potential anti–HIV agents: Asymmetric synthesis and structure–activity relationships," *J. Med. Chem.*, 36(5):519–528 (Mar. 5, 1993).

(List continued on next page.)

Primary Examiner—Amelia A. Owens
(74) Attorney, Agent, or Firm—Sherry M. Knowles, Esq.; King & Spalding, LLP

(57) ABSTRACT

Disclosed are novel processes for preparing 1,3-dioxolane nucleosides of general formula I and II:

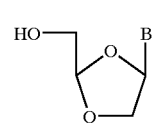

I

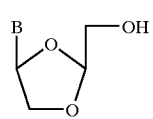

II wherein B is a purine or pyrimidine base or an analog or derivative thereof. The invention also provides intermediates for use in the preparation of these compounds.

17 Claims, 1 Drawing Sheet

OTHER PUBLICATIONS

Kornblum, N., et al., "A new and selective method of oxidation. The conversion of alkyl halides and alkyl tosylates to aldehydes," *J. Am. Chem. Soc.*, 81:4113–4114 (Aug. 5, 1959).

Kraus, J.–L., et al., "Synthesis of new 2,5–substituted 1,3–oxathiolanes. Intermediates in nucleoside chemistry," *Synthesis*, 1991:1046–1048 (Nov. 1991).

Marshall, J. A., et al., "Stereoselective total synthesis of the pseudopterolide kallolide A," *J. Org. Chem.*, 63(17):5962–5970 (1998).

Mewshaw, J.P., et al., "Dioxolane guanosine, the active form of the prodrug diaminopurine dioxolane, is a potent inhibitor of drug–resistant HIV–1 isolates from patients for whom standard nucleoside therapy fails," *J. Acquir. Immune Defic. Syndr.*, 29(1):11–20 (Jan. 1, 2002).

Norbeck, D. W. et al., "A new 2',3'–dideoxynucleoside prototype with in vitro activity against HIV," *Tetrahedron Letters*, 30(46):6263–6266 (1989).

Ohle, H., "Die Benzoylierung des Erythrits and Darstellung von Derivaten des O–Benzoyl–glykolaldehyds," *Chem. Ber.*, 74(2):291–294 (1941).

Shiao, M.–J., et al., "A convenient synthesis of protected α–hydroxyacetaldehydes," *Synthetic Commun.*, 18(4):359–366 (1988).

Sheikh, M.Y., "The vapor phase oxidation of alcohols by cupric oxide. A convenient preparation of aldehydes and ketones," *Tetrahedron Lett.*, 1972(4):257–260 (1972).

PROCESSES FOR PREPARING 1,3-DIOXOLANE NUCLEOSIDES

CROSS-REFERENCE TO RELATED APPLICATIONS

This application claims priority to U.S. Provisional Application No. 60/401,655, filed on Aug. 6, 2002, the disclosure of which is incorporated herein by reference.

FIELD OF THE INVENTION

This application is in the area of pharmaceutical chemistry and in particular provides processes for preparing 1,3-dioxolane-nucleosides, including in enantiomerically pure D- and L-form.

BACKGROUND OF THE INVENTION

AIDS, Acquired Immune Deficiency Syndrome, is a catastrophic disease that has reached global proportions. AIDS was first brought to the attention of the Center for Disease Control and Prevention (CDC) in 1981 when seemingly healthy homosexual men came down with Karposi's Sarcoma (KS) and *Pneumocystis carinii* pneumonia (PCP), two opportunistic diseases that were only known to afflict immunodeficient patients. A couple of years later, the causative agent of AIDS, a lymphoadenopathy-associated retrovirus, the human immunodeficiency virus (HIV) was isolated by the Pasteur Institute in Paris, and later confirmed by an independent source in the National Cancer Institute in the United States.

Another virus that causes a serious human health problem is the hepatitis B virus (HBV). HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a 2- to 6-month incubation period in which the host is unaware of the infection, HBV infection can lead to acute hepatitis and liver damage, resulting in abdominal pain, jaundice and elevated blood levels of certain enzymes. HBV can cause fulminant hepatitis, a rapidly progressing, often fatal form of the disease in which large sections of the liver are destroyed.

Patients typically recover from the acute phase of HBV infection. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, the high-risk group for HBV infection includes those in contact with HBV carriers or their blood samples. The epidemiology of HBV is very similar to that of AIDS, which is a reason why HBV infection is common among patients infected with HIV or AIDS. However, HBV is more contagious than HIV.

In 1985, it was reported that the synthetic nucleoside 3'-azido-3'-deoxythymidine AZT, Zidovudine, Retrovir) inhibits the replication of HIV and became the first FDA-approved drug to be used in the fight against AIDS. Since then, a number of other synthetic nucleosides, including 2',3'-dideoxyinosine (DDI), 2',3'-dideoxycytidine (DDC), 2',3'-dideoxy-2',3'-didehydrothymidine (D4T), (−)-2',3'-dideoxy-3'-thiacytidine (3TC), and (−)-carbocyclic 2',3'-didehydro-2',3'-dideoxyguanosine (carbovir) and its prodrug abacavir, have been proven to be effective against HIV. After cellular phosphorylation to the 5'-triphosphate by cellular kinase, these synthetic nucleosides are incorporated into a growing strand of viral DNA, causing chain termination due to the absence of the 3'-hydroxyl group. They can also inhibit the viral enzyme reverse transcriptase.

Both and 3TC and its 5-fluorocytosine analog (FTC) exhibit activity against HBV. Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" *Antimicrobial Agents and Chemotherapy*, December 1992, pp. 2686–2692; and Cheng, et al., *Journal of Biological Chemistry*, Volume 267(20), pp.13938–13942 (1992).

The discovery that a racemic oxathiolane nucleoside BCH-189 possessed a potent activity against replication of human immunodeficiency virus (HIV) (Belleau, B. et al., 5th International Conference on AIDS, Montreal, Canada, Jun. 4–9, 1989, #T.C.O. 1) prompted Chu et al. to synthesize the chiral products (+)- and (−)-BCH-189 (*Tetrahedron Lett.*, 1991, 32, 3791). The latter, lamivudine, otherwise known as 3TC or epivir, is currently used clinically in the treatment of both HIV infection and HBV infection. 3TC and interferon are currently the only FDA-approved drugs for the treatment of HBV infection. Viral resistance typically develops within 6 months of 3TC treatment in about 14% of patients.

It was later determined that the 5-fluorocytosine analogue, (−)-FTC, is even more active against HIV (Choi, W. et al., *J. Am. Chem. Soc.*, 1991, 113, 9377). More recently, the racemic form of FTC or Racivir has been discovered to show more beneficial effects against HIV or HBV than (−)-FTC alone (Schinazi, R. F., et al., *Antimicrobial Agents Chemotherapy* 1992, 2423, U.S. Pat. Nos. 5,204,4665; 5,210,085; 5,914,331; 639,814). Cis-2-hydroxymethyl-5-(5-fluorocytosin-1-yl)-1,3-oxathiolane (FTC) is currently in clinical trials for the treatment of HIV and separately for HBV. See Schinazi, et al., (1992) "Selective inhibition of human immunodeficiency viruses by racemates and enantiomers of cis-5-fluoro-1-[2-(hydroxymethyl)-1,3-oxathiolane-5-yl]cytosine" *Antimicrob. Agents Chemother.* 2423–2431; U.S. Pat. No. 5,210,085; WO 91/11186; WO 92/14743; U.S. Pat. No. 5,914,331 and U.S. Pat. No. 5,814,639.

These 1,3-oxathiolane nucleosides are manufactured by condensation of silylated purine or pyrimidine base with a 1,3-oxathiolane intermediate. U.S. Pat. No. 5,204,466 discloses a method to condense a 1,3-oxathiolane with a silylated pyrimidine using tin chloride as a Lewis acid, which provides virtually complete β-stereoselectivity (see also Choi et al., loc. cit.). A number of U.S. patents disclose processes for the preparation of 1,3-oxathiolane nucleosides via condensation of a 1,3-oxathiolane-2carboxylic acid ester with a protected silylated base in the presence of a silicon-based Lewis acid, followed by reduction of the ester to the corresponding hydroxymethyl group to afford the final product (see U.S. Pat. Nos. 5,663,320; 5,693,787; 5,696,254; 5,744,596; 5,756,706 and 5,864,164). In addition, these patents contain generic disclosures for the synthesis of 1,3-dioxolane nucleosides in a similar fashion using the corresponding 1,3-dioxolane intermediate.

U.S. Pat. No. 5,272,151 discloses a process using a 2-O-protected-5-O-acylated-1,3-oxathiolane for the preparation of nucleosides by condensation with a silylated purine or pyrimidine base in the presence of a titanium catalyst.

U.S. Pat. No. 6,215,004 discloses a process for producing 1,3-oxathiolane nucleosides that includes condensing 2-O-protected-methyl-5-chloro-1,3-oxathiolane with a silylated 5-fluorocytosine without a Lewis acid catalyst.

In all cases, the 1,3-oxathiolane ring is prepared in one of the following ways: (i) reaction of an aldehyde derived from a glyoxylate or glycolic acid with mercaptoacetic acid in toluene in the presence of p-toluenesulfonic acid to give 5-oxo-1,3-oxathiolane-2-carboxylic acid (Kraus, J-L., et al., *Synthesis*, 1991, 1046); (ii) cyclization of anhydrous glyoxylates with 2-mercaptoacetaldehyde diethylacetal at reflux in toluene to give 5-ethoxy-1,3-oxathiolane lactone (U.S. Pat. No. 5,047,407); (iii) condensation of glyoxylic acid ester with mercaptoacetaldehyde (dimeric form) to give 5-hydroxy-1,3-oxathiolane-2-carboxylic ester or (iv) coupling of an acyloxyacetaldehyde with 2,5-dihydroxy-1,4-dithiane, the dimeric form of 2-mercaptoacetaldehyde to form a 2-(ayloxy)methyl-5-hydroxy-1,3-oxathiolane. The lactone, 5-oxo compound, has to be reduced to the corresponding lactol during the process to synthesize nucleosides. The 2-carboxylic acid or its ester also has to be reduced to the corresponding 2-hydroxymethyl derivatives with borane-methylsulfide complex.

The key intermediate, aldehyde, can be prepared using several methods: (i) lead tetraacetate oxidation of 1,4-di-O-benzoyl meso-erythritol (Ohle, M., Ber., 1941, 74, 291), 1,6-di-O-benzoyl D-mannitol (Hudson, C. S., et al., *J. Am. Chem. Soc.*, 1939, 61, 2432) or 1,5-di-O-benzoyl-D-arabitol (Haskins, W. T., et. al., *J. Am. Chem. Soc.*, 1943, 65, 1663); (ii) preparation of monoacylated ethylene glycol followed by oxidation to aldehyde (Sheikh, E., *Tetrahedron Lett.*, 1972, 257; Mancuso, A. J. and Swern, D., *Synthesis*, 1981, 165; Bauer, M., *J. Org. Chem.*, 1975, 40, 1990; Hanessian, S., et al., *Synthesis*, 1981, 394); (iii) acylation of ethylene chlorohydrin followed by dimethylsulfoxide oxidation (Kornblum, N., et al., *J. Am. Chem. Soc.*, 1959, 81, 4113); (iv) acylation of 1,2-isopropylideneglycerol followed by deacetonation and periodate oxidation (Shao, M-J., et al., *Synthetic Commun.*, 1988, 18, 359; Hashiguchi, S., et al, *Heterocycles*, 1986, 24, 2273); (v) lead tetraacetate oxidation (Wolf, F. J., Weijlard, J., *Org. Synth., Coll. Vol.*, 1963, 4, 124); (vi) ozonolysis of allyl or 3-methyl-2-buten-1-ol acylate (Chou, T.-S., et al., *J. Chin. Chem. Soc.*, 1997, 44, 299; Hambeck, R., Just, G.; *Tetrahedron Lett.*, 1990, 31, 5445); (vii) and more recently, by acylation of 2-butene-1,4-diol followed by ozonolysis (Marshall, J. A., et al., *J. Org Chem.*, 1998, 63, 5962). Also, U.S. Pat. No. 6,215,004 discloses a process to prepare acyloxyacetaldehyde diethylacetal by acylation of 2,2-diethoxyethanol.

α-Acyloxyacetaldehyde is the key intermediate not only for the synthesis of those oxathiolane and dioxolane nucleosides but also for the synthesis of biologically active compounds, such as mescarine (Hopkins, M. H., et al., *J. Am. Chem. Soc.*, 1991, 113, 5354), oxetanocin (Hambalek, R., Just, J., *Tetrahedron Lett.*, 1990, 31, 5445), kallolide A (Marshall, J. A., et al *J. Org. Chem.*, 1998, 63, 5962), (±)-kumausallene and (+)-epi-Kumausallene (Grese, T. S., et al., *J. Org. Chem.*, 1993, 58, 2468), 1,3-dioxolane nucleosides.

Norbeck, D. W. et al. (Tetrahedron Letters 1989, 30, 6263) reported a synthesis of (±)-1-[(2β,4β)-2-(hydroxymethyl)-4-dioxolanyl]thymine ("(±)-dioxolane-T") that results in a racemic mixture of diastereomers at the C4' atom. The product is a derivative of 3'-deoxythymidine in which the C3' atom has been replaced by an O3' atom. The product was synthesized in five steps from benzyloxyaldehyde dimethylacetal and (±)-methyl glycerate, resulting in a 79% yield of the 1:1 diastereomeric mixture. Norbeck reported that the racemic mixture of (±)-dioxolane-T showed moderate anti-HIV activity in ATH8 cells ($EC_{50}$ of 20 μM; Tetrahedron Letters 1989, 30, 6246).

Belleau et al. (5th International Conference on AIDS; Montreal, Canada; Jun. 4–9, 1990; Paper No. TCO1) reported a method of synthesizing cytidine nucleosides that contain oxygen or sulfur in the 3'-position. The dioxolane ring was prepared by condensation of $RCO_2CH_2CHO$ with glycerin. As with Norbeck's procedure, the Belleau synthesis results in a racemic mixture of diastereomers about the C4' carbon of the nucleoside. Belleau reported that the sulfur analog, referred to as (±)-BCH-189, had anti-HIV activity. (±)-Dioxolane-T was also synthesized in similar fashion by Choi et al. (Choi, W.-B et al., J. Am. Chem. Soc. 1991, 113, 9377–9378; Liotta, D. C. et al. U.S. Pat. No. 5,852,027).

An asymmetric synthesis of dioxolane nucleosides was reported by Evans, C. A. et al. (Tetrahedron: Asymmetry 1993, 4, 2319–2322). Reaction of D-mannitol with $BnOCH_2CH-(OCH_3)_2$ in the presence of $SnCl_2$ in 1,2-dimethoxyethane followed by $RuCl_3/NaOCl$ oxidation gave cis- and trans-dioxolane-4-carboxylic acid, which was then converted to D- and L-dioxolane nucleosides by decarboxylation, coupling and deprotection reactions. An alternative and more efficient route to these carboxylic acids by reaction of $BnOCH_2CH(OCH_3)_2$ with L-ascorbic acid was also reported in the paper.

The chiral carboxylic acid (6) can also be prepared by reacting commercially available 2,2-dimethyl-1,3-dioxolane-4-(S)-carboxylic acid with a protected derivative of hydroxy-acetaldehyde such as benzoyloxyacetaldehyde, under acidic conditions (Mansour, T. et al, U.S. Pat. No. 5,922,867; Nghe Nguyen-Ba, U.S. Pat. No. 6,358,963).

The antiviral activity of dioxolane nucleosides (see Corbett, A. H. & Rublein J. C., Curr. Opin. Investig. Drugs 2001, 2, 348–353; Gu, Z., et al., Antimicrob. Agents Chemother. 1999, 43, 2376–2382; Gu, Z., et al., Nucleosides Nucleotides 1999, 18, 891–892) prompted Chu et al. to synthesize a series of analogs enantiomerically in a search for potent antiviral and/or anticancer agents. Among them, several compounds such as (−)-(2'R,4'R)-2,6-diamino-9-[2-(hydroxy-methyl)-1',3'-dioxolan-4'yl]purine (DAPD) (U.S. Pat. No. 5,767,122), (−)-(2S,4R)-1-[2-(hydroxymethyl)-1,3-dioxolan-4yl]cytosine) L-OddC) and (−)-(2'S,4'R)-1'-[2'-(hydroxy-methyl)-1',3'-dioxolan-4'-yl]-5-iodouracil) L-IOddU (U.S. Pat. No. 5,792,773) have been identified and are currently in pre-clinical or clinical studies to assess their value as antiviral or anticancer agents (see Kim, H.-O. et al., J. Med. Chem. 1993, 36, 519–528 and references therein; Corbett, A. H. & Rublein J. C., Curr. Opin. Investig. Drugs 2001, 2, 348–353; Gu, Z., et al., Antimicrob. Agents Chemother. 1999, 43, 2376–2382; Mewshaw, J. P., et al., J. Acquir. Immune Defic. Syndr. 2002, 29, 11–20).

As one enantiomer of racemic nucleosides usually shows higher biological activity (see Kim et al., J. Med. Chem. 1993, 36, 519–528 and references therein), Chu et al. developed methods for the asymmetric synthesis of dioxolane nucleosides from D-mannose and L-gulonic lactone for D- and L-dioxolane nucleosides, respectively (U.S. Pat. Nos. 5,767,122, 5,792,773). However, these processes involved many steps and most of the intermediates needed to be purified by silica gel column chromatography (see Kim et al. J. Med. Chem. 1993, 36, 519–528 and references therein).

To prepare a sufficiently large quantity of dioxolane nucleoside drug substance for clinic trials, a chiral 2-acyloxymethyl-5-oxo-1,3-dioxolane has been used as the key intermediate. It was prepared by cyclization of ROCH$_2$CHO or its acetal with glycolic acid in the presence of BF$_3$, followed by column separation on chiral resin or by enzymatic resolution. It is very expensive to prepare the chiral lactone by these processes, because of the high cost of the chiral resin and enzymes.

Thus, there remains a need for cost-effective and stereoselective processes to produce biologically active isomers of dioxolane nucleosides.

It is an object of the present invention to provide novel and cost-effective processes for the synthesis of enantiomerically pure dioxolane nucleosides.

SUMMARY OF THE INVENTION

The present invention includes an efficient synthetic route to 1,3-dioxolane nucleosides from inexpensive precursors, with the option of introducing functionality as needed. These processes allow the stereoselective preparation of the biologically active isomer of these compounds.

In one embodiment of the present invention, a process for preparing a D- or L-1,3-dioxolane nucleosides is provided, comprising:

a) preparing or obtaining a cyclized compound of the formula (VII) or (VIII):

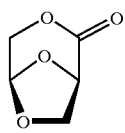

(VII)

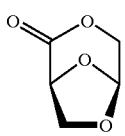

(VIII)

and then b) opening the ring of the compound of formula (VII) or (VIII) and protecting, if necessary, to obtain a compound of formula 6a or 6b:

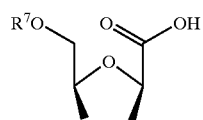

(6a)

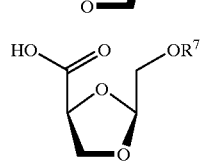

(6b)

wherein R$^7$ is a suitable oxygen protecting group, and then c) activating the compound of formula 6a or 6b, to obtain a compound of formula 7a or 7b:

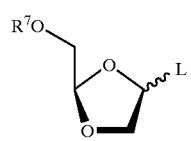

(7a)

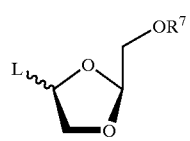

(7b)

wherein L is a suitable leaving group, such as an O-acyl, such as OAc, halogen (F, Br, Cl, I) or OMs, OTs, and the like; and then d) coupling the compound of formula 7a or 7b, to an activated and/or protected purine or pyrimidine base or its derivative to obtain a compound of formula 8a or 8b:

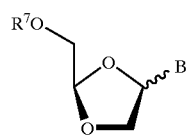

(8a)

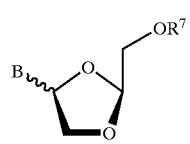

(8b)

wherein B is a purine or pyrimidine base or its derivative; and then e) deprotecting the compound of formula 8a or 8b, if necessary, to give a 1,3-dioxolane nucleoside.

In one particular embodiment of the present invention, a process for preparing the cyclized compound of the formula VII or VIII is provided, comprising:

a) preparing or obtaining a compound of the formula 1 or 1' (both including D- and L-isomers):

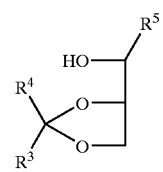

(1)

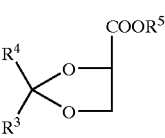

(1')

wherein R$^3$ and R$^4$ are independently alkyl or aralkyl;
R$^5$ is =CR$^{5'}$ or CH(OH)R$^{5'}$; and
R$^{5'}$ is alkyl or aralkyl; and then b) oxidizing the compound of the formula 1 or hydrolyzing the compound of the formula 1' to obtain a compound of formula 2 (including D- and L-isomers):

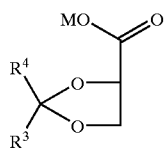

(2)

wherein M is a metal, preferably an alkali metal, such as Na or K; and then c) coupling the compound of the formula 2 with X'—CH$_2$CH(OR$^6$)$_2$, wherein X' is a suitable leaving group, preferably a halogen (F, Cl, Br, I) or MsO, TsO or the like, and most preferably Br, to obtain a compound of formula 3 (including D- and L-isomers):

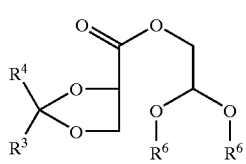

(3)

wherein each R$^6$ is independently an alkyl or aralkyl; and then d) hydrolyzing the compound of the formula 3 to obtain a compound of formula 4 (including D- and L-isomers):

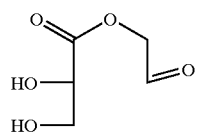

(4)

and then e) cyclizing the compound of the formula 3 or 4 to obtain the cyclized compound of the formula VII or VIII.

In an even more preferred embodiment, the cyclization of the compound of the formula 3 or 4 is achieved in acidic conditions.

Therefore, the processes of the present invention may be used to prepare compounds of formulae III to VI:

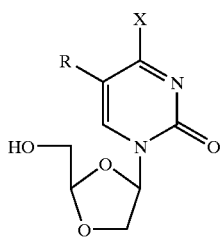

III

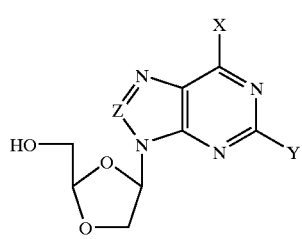

IV

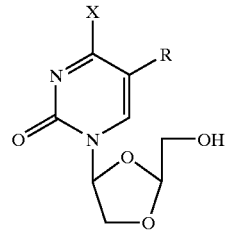

V

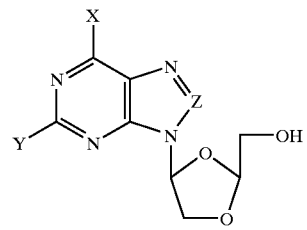

VI and pharmaceutically acceptable salts or esters thereof, wherein:

R is H, halogen (F, Cl, Br, I), OH, OR' (R' is lower alkyl of $C_1$–$C_4$), OCH$_3$, SH, SR', SCH$_3$, NH$_2$, NHR', NR'$_2$, lower alkyl of $C_1$–$C_4$, CH$_3$, CH=CH$_2$, N$_3$C=CH$_2$, CO$_2$H, CO$_2$R', CONH$_2$, CONHR', CH$_2$OH, CH$_2$CH$_2$OH, CF$_3$, CH$_2$CH$_2$F, CH=CHCO$_2$H, CH=CHCO$_2$R', CH=CHCl, CH=CHBr, or CH=CHI;

each X and Y are independently H, halogen (F, Cl, Br, I), OH, OR' (R' is lower alkyl of $C_1$–$C_4$), OCH$_3$, SH, SR', SCH$_3$, NH$_2$, NHR', NR'$_2$, or CH$_3$; and Z is CH, C—X (X is defined as above).

The processes of the present invention may be used to prepare intermediates of formulae VII and VIII:

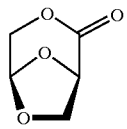

(VII)

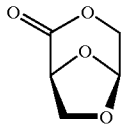

(VIII)

DETAILED DESCRIPTION OF THE INVENTION

Figure 1:
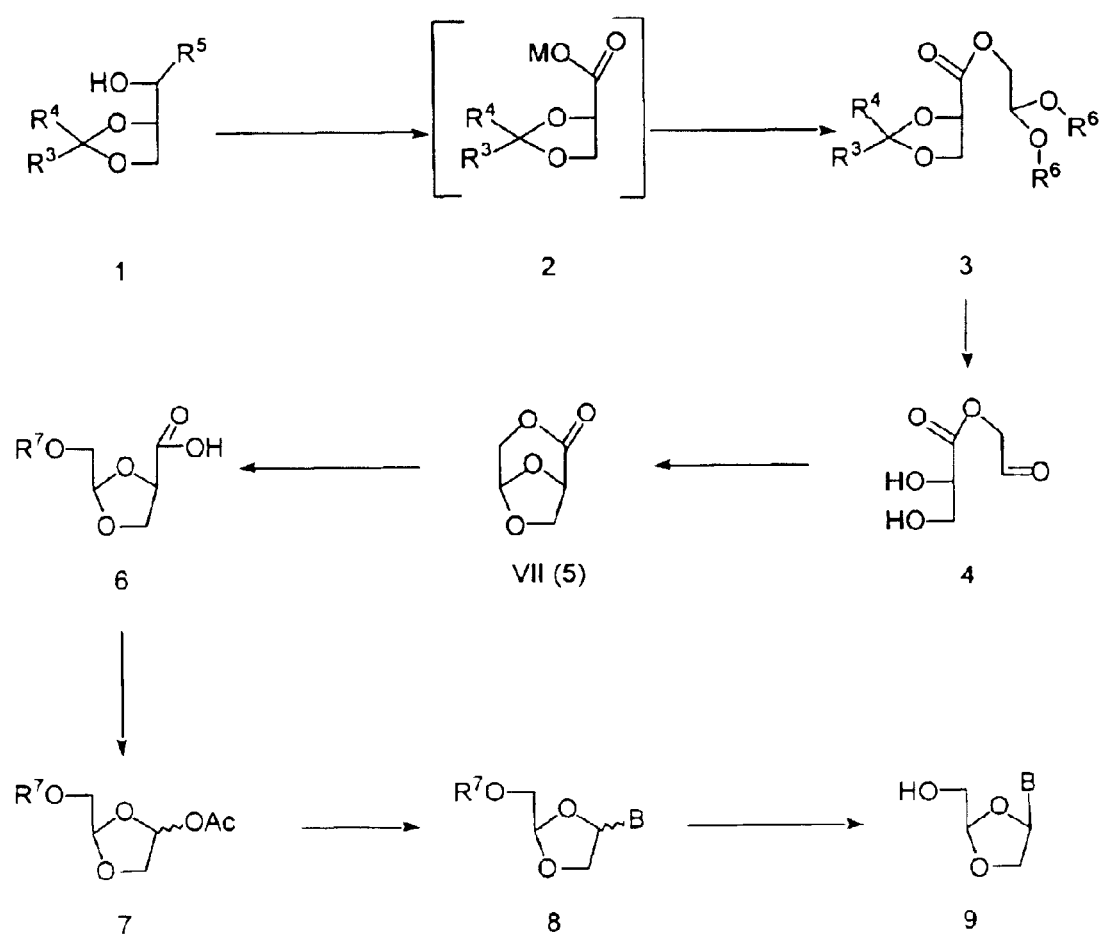
FIG. 1 is a non-limiting illustration of the asymmetric synthesis of dioxolane nucleosides through intermediate bicyclic ester VII or VIII. All intermediates of 1 to 9 include D- and L-isomers.

The present invention includes an efficient synthetic routes to 1,3-dioxolane nucleosides from inexpensive precursors, with the option of introducing functionality as needed. These processes allow the stereoselective preparation of the biologically active isomer of these compounds.

In one embodiment of the present invention, a process for preparing a D- or L-1,3-dioxolane nucleosides is provided, comprising:

a) preparing or obtaining a cyclized compound of the formula VII or VIII:

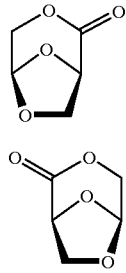

(VII)

(VIII)

and then b) opening the ring of the compound of formula VII or VIII and protecting, if necessary, to obtain a compound of formula 6a or 6b:

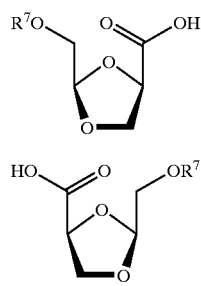

(6a)

(6b)

wherein $R^7$ is a suitable oxygen protecting group, and then c) activating the compound of formula 6a or 6b, to obtain a compound of formula 7a or 7b:

(7a)

(7b)

wherein L is a suitable leaving group, such as an O-acyl, such as OAc, or halogen (F, Br, Cl or I) or MsO, TsO and the like; and then d) coupling the compound of formula 7a or 7b, to an activated and/or protected purine or pyrimidine base or its derivative to obtain a compound of formula 8a or 8b:

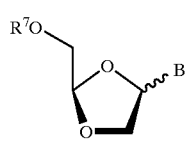

(8a)

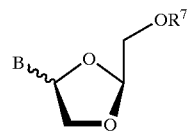

(8b)

wherein B is a purine or pyrimidine base or its derivative; and then e) deprotecting the compound of formula 8a or 8b, if necessary, to give a 1,3-dioxolane nucleoside.

In one particular embodiment of the present invention, a process for preparing the cyclized compound of the formula VII or VIII is provided, comprising:

a) preparing or obtaining a compound of the formula 1 or 1' (both including D- and L-isomers):

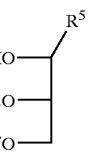

(1)

(1')

wherein $R^3$ and $R^4$ are independently alkyl or aralkyl; $R^5$ is $=CR^{5'}$ or $CH(OH)R^{5'}$; and $R^{5'}$ is alkyl or aralkyl; and then b) oxidizing the compound of the formula 1 or hydrolyzing the compound of the formula 1' to obtain a compound of formula 2 (including D- and L-isomers):

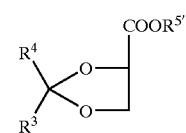

(2)

wherein M is a metal, preferably an alkali metal, such as Na or K; and then c) coupling the compound of the formula 2 with $X'$—$CH_2CH(OR^6)_2$, wherein X' is a suitable leaving group, preferably a halogen (F, Cl, Br, I), or MsO, TsO or the like, and most preferably Br, to obtain a compound of formula 3 (including D- and L-isomers):

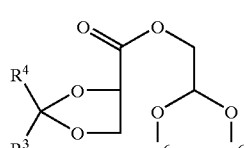

(3)

wherein each $R^6$ is independently an alkyl or aralkyl; and then d) hydrolyzing the compound of the formula 3 to obtain a compound of formula 4 (including D- and L-isomers):

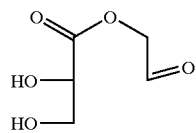
(4)

and then e) cyclizing the compound of the formula 3 or 4 to obtain the cyclized compound of the formula VII or VIII.

In an even more preferred embodiment, the cyclization of the compound of the formula 3 or 4 is achieved in acidic conditions.

Therefore, the processes of the present invention may be used to prepare compounds of formulae III to VI:

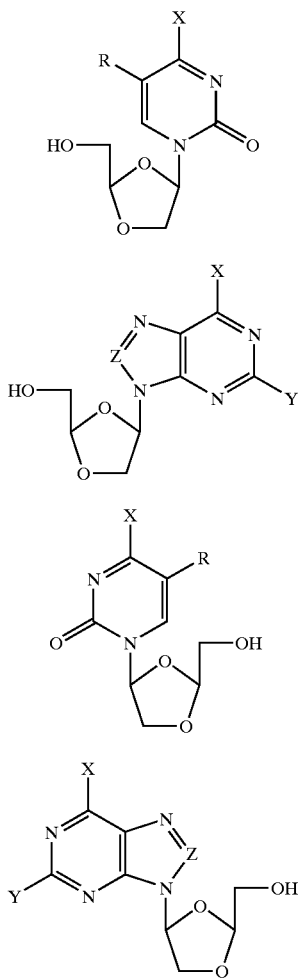

and pharmaceutically acceptable salts or esters thereof, wherein:

R is H, halogen (F, Cl, Br, I), OH, OR' (R' is lower alkyl of $C_1$–$C_4$), $OCH_3$, SH, SR', $SCH_3$, $NH_2$, NHR', $NR'_2$, lower alkyl of $C_1$–$C_4$, $CH_3$, $CH=CH_2$, $N_3C=CH_2$, $CO_2H$, $CO_2R'$, $CONH_2$, CONHR', $CH_2OH$, $CH_2CH_2OH$, $CF_3$, $CH_2CH_2F$, $CH=CHCO_2H$, $CH=CHCO_2R'$, $CH=CHCl$, $CH=CHBr$, or $CH=CHI$;

each X and Y are independently H, halogen (F, Cl, Br, I), OH, OR' (R' is lower alkyl of $C_1$–$C_4$), $OCH_3$, SH, SR', $SCH_3$, $NH_2$, NHR', $NR'_2$, or $CH_3$; and Z is CH, or C—X (X is defined as above).

The processes of the present invention may be used to prepare intermediates of formulae VII and VIII:

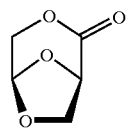
(VII)

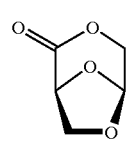
(VIII)

The process involves oxidation of 1,2-O-protected-glyceral, or its analog or derivative to a 1,2-O-protected-glyceric acid salt, such as potassium, sodium or other alkali metal. These salts also can be prepared by hydrolyzing commercially available intermediates, methyl (R)- or (S)-1,2-O-isopropylidene-glycerate with base, such as aqueous KOH, NaOH and the like. The salt reacts with X'—$CH_2CH(OR^6)_2$, wherein X' is a suitable leaving group, preferably a halogen (F, Cl, Br, I) such as $BrCH_2CH(OR^6)_2$ or its derivative, or MsO, or TsO and the like, followed by cyclization to give the bicyclic intermediate (VII) or (VIII), which can then be used for the preparation of enantiomerically pure D- or L-dioxolane nucleosides.

Definitions

As used herein, the term "substantially free of," "substantially in the absence of" or "isolated" refers to a nucleoside composition that includes at least 95%, and preferably 99% to 100% by weight, of the designated enantiomer of that nucleoside. In a preferred embodiment, the process produces compounds that are substantially free of enantiomers of the opposite configuration.

The term alkyl, as used herein, unless otherwise specified, refers to a saturated straight, branched, or cyclic, primary, secondary, or tertiary hydrocarbon of $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term aryl, as used herein, and unless otherwise specified, refers to phenyl, biphenyl, or naphthyl. The term includes both substituted and unsubstituted moieties. The aryl group can be substituted with one or more moieties selected from the group consisting of bromo, chloro, fluoro, iodo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes bromo, chloro, fluoro, and iodo.

The term heteroatom, as used herein, refers to oxygen, sulfur, nitrogen, and phosphorus.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term purine or pyrimidine base includes, but is not limited to, adenine, $N^6$-alkyl-purines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluoro-cytosine, 5-methylcytosine, 6-azapyrimidine, including 6-azacytosine, 2- and/or 4-mercapto-pyrmidine, uracil, 5-halouracil, including 5-fluorouracil, $C^5$-alkylpyrimidines, $C^5$-benzyl-pyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amido-pyrimidine, $C^5$-cyanopyrimidine, $C^5$-nitro-pyrimidine, $C^5$-aminopyrimidine, $N^2$-alkyl-purines, $N^2$-alkyl-6-thiopurines, 5-azacytidinyl, 5-azauracilyl, triazolopyridinyl, imidazolo-pyridinyl, pyrrolopyrimidinyl, and pyrazolopyrimidinyl. Purine bases include, but are not limited to, guanine, adenine, hypoxanthine, 2,6-diaminopurine, 2-(Br, Fl, Cl or I)-purine optionally with a substituent including an amino or carbonyl group in the 6-position, and 6-(Br, Cl, or I)-purine optionally with a substituent including an amino or carbonyl group in the 2-position. Functional oxygen and nitrogen groups on the base can be protected as necessary or desired. Suitable protecting groups are well known to those skilled in the art, and include trimethylsilyl, dimethylhexylsilyl, t-butyldimethylsilyl, t-butyldiphenylsilyl, trityl, alkyl groups, and acyl groups such as acetyl and propionyl, methanesulfonyl, and p-toluenesulfonyl.

The term heteroaryl or heteroaromatic, as used herein, refers to an aromatic that includes at least one sulfur, oxygen, nitrogen or phosphorus in the aromatic ring. The term heterocyclic refers to a nonaromatic cyclic group wherein there is at least one heteroatom, such as oxygen, sulfur, nitrogen or phosphorus in the ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyl-diphenylsilyl, trityl or substituted trityl, alkyl groups, acyl groups such as acetyl and propionyl, methanesulfonyl, and p-toluenylsulfonyl.

These purine or pyrimidine bases, heteroaromatics and heterocycles can be substituted with alkyl groups or aromatic rings, bonded through single or double bonds or fused to the heterocycle ring system. The purine base, pyrimidine base, heteroaromatic, or heterocycle may be bound to the sugar moiety through any available atom, including the ring nitrogen and ring carbon (producing a C-nucleoside).

DETAILED DESCRIPTION OF PROCESS STEPS

Process for Manufacturing β-D- or β-L-1,3-Dioxolane Nucleoside via a Cyclized Intermediate Step One—Preparation of Cyclized Intermediate The key starting material for this process is an appropriately substituted D- or L-cyclic intermediate. The D- or L-cyclic intermediate can be purchased or can be prepared by any known means including standard elimination or oxidation and reduction techniques. In one embodiment, the D- or L-cyclic intermediate is prepared according to the following protocol.

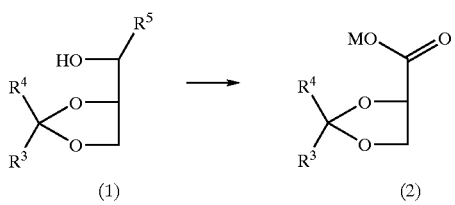

(1) → (2)

wherein $R^3$ and $R^4$ are independently alkyl or aralkyl;
$R^5$ is =$CR^{5'}$ or $CH(OH)R^{5'}$; $R^{5'}$ is alkyl or aralkyl; and
M is a metal, preferably an alkali metal, such as Na or K.

A glycerol is oxidized to a 1,2-O-protected-glyceric acid salt (2) by reacting a 1,2-O-protected-glycerol (1) or glycerol analog, such as D- or L-1,2-O-diisopropylideneglycerol or 1,2:5,6-di-O-diisopropylidene-D-mannitol or other vicinal-protected diol, in a compatible solvent at a suitable temperature with the appropriate oxidizing agent to yield the corresponding a 1,2-O-protected-glyceric acid salt (2). The protected glycerol can be purchased or can be prepared by any known means including standard protection techniques. The glycerol can be protected with any suitable protecting group, such as with an acyl or silyl group, though preferably with an acyl group, by methods well known to those skilled in the art, as taught in Greene, et al., Protective Groups in Organic Synthesis, John Wiley and Sons, Second Edition, 1991. For example, acetone may be reacted with the glycerol to form the corresponding D- or L-1,2-O-diisopropylideneglycerol at room temperature.

Possible oxidizing agents are any reagents that promote oxidation, including but are not limited to, $NaIO_4/RuCl_3$ hydrate, $NaOCl/RuCl_3$ hydrate or $KMnO_4$, or $NaIO_4$ or $KIO_4$ then $KMnO_4$.

Glyceric acid salt formation can be carried out at any temperature that achieves the desired results, i.e., that is suitable for the reaction to proceed at an acceptable rate without promoting decomposition or excessive side products. Preferred temperatures are from −10° C. to 100° C.

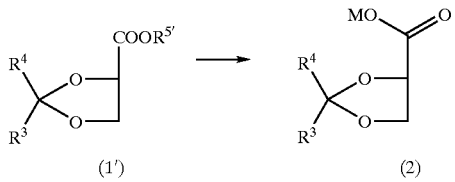

(1') → (2)

wherein $R^3$ and $R^4$ are independently alkyl or aralkyl;
$R^5$ is =$CR^{5'}$ or $CH(OH)R^{5'}$; $R^{5'}$ is alkyl or aralkyl; and
M is a metal, preferably an alkali metal, such as Na or K.

Compound 2 can be prepared by hydrolyzing 1' with base, such as aqueous KOH or NaOH.

Any reaction solvent can be selected that can achieve the necessary temperature and that can solubilize the reaction components. Nonlimiting examples are any aprotic solvent including, but not limiting to, alkyl solvents such as hexane and cyclohexane, toluene, acetone, ethyl acetate, THF, dioxane, acetonitrile, dichloromethane, dichloroethane, diethyl ether, dimethylformamide (DMF), dimethylsulfoxide (DMSO), dimethylacetamide or any combination thereof, or, in the alternative, water.

Compounds 1, 1' and 2 include D- and L-isomers.

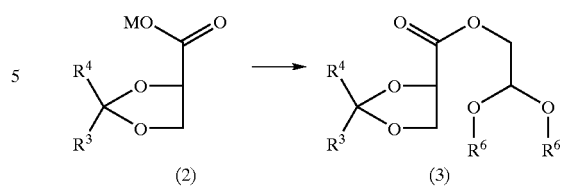

(2) → (3)

wherein each $R^6$ is independently a hydrogen, alkyl or aralkyl; wherein at most one $R^6$ is hydrogen.

The 1,2-O-protected-glyceric acid salt (2) can then be reacted with X'—$CH_2CH(OR^6)_2$, wherein X' is a suitable leaving group, preferably a halogen (F, Cl, Br, I) or MsO, TsO or the like, and most preferably Br, with or without a phase transfer catalyst, such as a crown ether or tetraalkylammonium halide, in a compatible solvent at a suitable temperature to yield the acetal or hemiacetal 3 (including D- and L-isomers). In one embodiment, the glyceric acid salt (2) is not purified from the previous step.

Acetal or hemiacetal formation can be carried out at any temperature that achieves the desired results, i.e., that is suitable for the reaction to proceed at an acceptable rate without promoting decomposition or excessive side products. Preferred temperatures are refluxing conditions.

Any reaction solvent can be selected that can achieve the necessary temperature and that can solubilize the reaction components. Nonlimiting examples are any aprotic solvent including, but not limiting to, alkyl solvents such as hexane and cyclohexane, toluene, dioxane, acetonitrile, dichloromethane, dichloroethane, dimethylformamide (DMF), dimethylsulfoxide (DMSO), dimethylacetamide or any combination thereof, preferably anhydrous DMF.

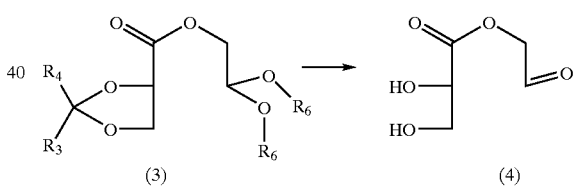

(3) → (4)

The acetal or hemiacetal 3 can then be hydrolyzed under acidic conditions in a compatible solvent at a suitable temperature to yield the aldehyde 4 (including D- and L-isomers). Suitable acids for the hydrolysis include aqueous acetic acid, formic acid, aqueous trifluoroacetic acid, aqueous sulfuric acid, aqueous hydrochloric acid, methanesulfonic acid, alkyl or aralkylsulfonic acid or a Lewis acid.

Aldehyde formation can be carried out at any temperature that achieves the desired results, i.e., that is suitable for the reaction to proceed at an acceptable rate without promoting decomposition or excessive side products. Preferred temperatures are from −10° C. to room temperature.

Any reaction solvent can be selected that can achieve the necessary temperature and that can solubilize the reaction components. Nonlimiting examples are any protic or aprotic solvent including, but not limiting to, alkyl solvents such as hexane and cyclohexane, toluene, THF, dioxane, acetonitrile, dichloromethane, dichloroethane, diethyl ether, dimethylformamide (DMF), dimethylsulfoxide (DMSO), dimethylacetamide or any combination thereof, or, in the alternative water.

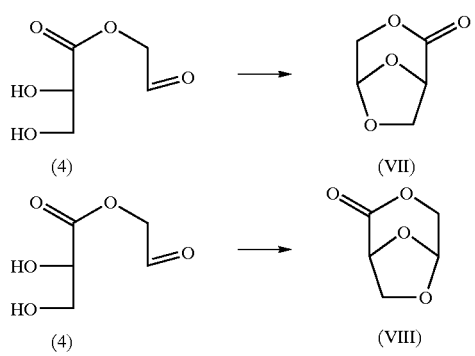

The D- or L-aldehyde 4 can then be cyclized, preferably in the presence of acid, in a compatible solvent at a suitable temperature to yield the key intermediate VII or VIII. Preferred acid is BF$_3$ etherate.

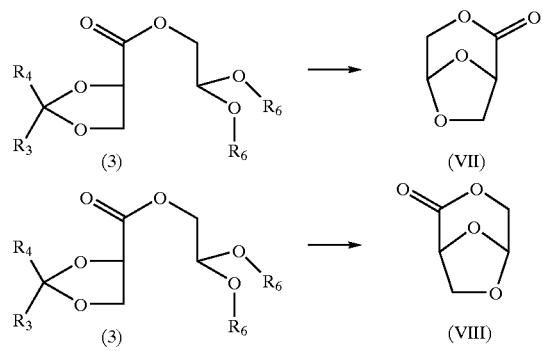

The D- or L-3 can also be cyclized, preferable in the presence of acid, in a compatible solvent at a suitable temperature to yield the key intermediate VII or VIII. In a preferred embodiment, the acid is BF$_3$ etherate.

The cyclization can be carried out at any temperature that achieves the desired results, i.e., that is suitable for the reaction to proceed at an acceptable rate without promoting decomposition or excessive side products. Preferred temperatures are from –10° C. to 100° C.

Any reaction solvent can be selected that can achieve the necessary temperature and that can solubilize the reaction components. Nonlimiting examples are any aprotic solvent including, but not limiting to, alkyl solvents such as hexane and cyclohexane, toluene, THF, dioxane, acetonitrile, dichloromethane, dichloroethane, diethyl ether, dimethylsulfoxide (DMSO), dimethylacetamide or any combination thereof, preferably acetonitrile.

Step Two—Preparation of Nucleoside

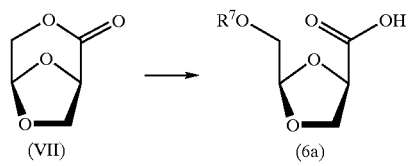

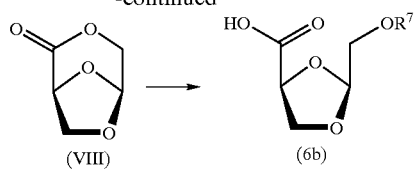

wherein R$^7$ is a suitable oxygen protecting group.

The key intermediate VII or VIII can then be hydrolyzed in the presence of an aqueous alkali or alkali earth metal base, such as aqueous NaOH or aqueous KOH, in a compatible solvent at a suitable temperature to yield the carboxylic acid, which then, can be protected, if necessary, by standard protection techniques to yield the appropriately protected carboxylic acid 6a or 6b. The carboxylic acid can be protected with any suitable protecting group, such as with an acyl or silyl group, though preferably with an acyl group, by methods well known to those skilled in the art, as taught in Greene, et al., Protective Groups in Organic Synthesis, John Wiley and Sons, Second Edition, 1991. For example, acetone may be reacted with the glycerol to form the corresponding D- or L-1,2-O-diisopropylideneglycerol at room temperature.

The carboxylic acid formation can be carried out at any temperature that achieves the desired results, i.e., that is suitable for the reaction to proceed at an acceptable rate without promoting decomposition or excessive side products. Preferred temperatures are from –10° C. to room temperature.

Any reaction solvent can be selected that can achieve the necessary temperature and that can solubilize the reaction components. Nonlimiting examples are any aprotic solvent including, but not limiting to, alkyl solvents such as hexane and cyclohexane, toluene, ethyl acetate, THF, dioxane, acetonitrile, dichloromethane, dichloroethane, diethyl ether, dimethylformamide (DMF), dimethylsulfoxide (DMSO), dimethylacetamide or any combination thereof, or in the alternative, water.

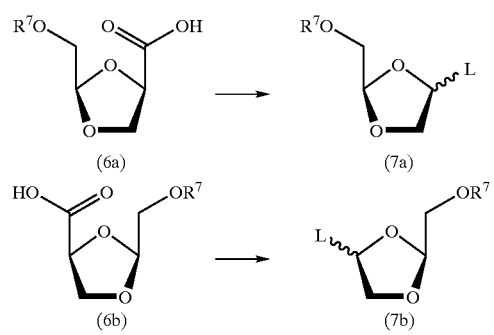

wherein L is a suitable leaving group, such as an O-acyl, such as OAc, or halogen (F, Br, Cl or I) or OMs, OTs, or the like.

The appropriately protected carboxylic acid 6a or 6b can then be activated, in a compatible solvent at a suitable temperature, to obtain an activated 1,3-dioxolane 7a or 7b. For example, the appropriately protected carboxylic acid (6a) or (6b) can be decarboxylated with lead tetraacetate to give a 1,3-dioxolane 4-acetate 7.

The decarboxylation can be carried out at any temperature that achieves the desired results, i.e., that is suitable for the reaction to proceed at an acceptable rate without promoting decomposition or excessive side products. Preferred temperatures are from –10° C. to 100° C.

Any reaction solvent can be selected that can achieve the necessary temperature and that can solubilize the reaction components. Nonlimiting examples are any aprotic solvent including, but not limiting to, alkyl solvents such as hexane and cyclohexane, toluene, ethyl acetate, THF, dioxane, acetonitrile, dichloromethane, dichloroethane, diethyl ether, pyridine, dimethylformamide (DMF), dimethylsulfoxide (DMSO), dimethylacetamide or any combination thereof, preferably anhydrous acetonitrile.

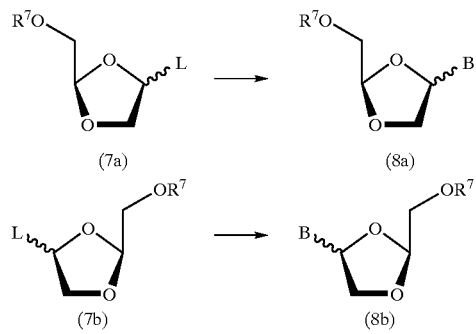

wherein B is a purine or pyrimidine base or its derivative.

The activated 1,3-dioxolane 7a or 7b can then be coupled to the purine or pyrimidine base or its derivative in a compatible solvent at a suitable temperature, using any means known in the art, to obtain a protected β-D- or β-L-1,3-dioxolane nucleoside 8a or 8b. For example, an activated purine or pyrimidine base, preferably via silylation of the base, such as a base silylated with HMDS, can be coupled to the 1,3-dioxolane using a Lewis acid, such as tin tetrachloride, titanium tetrachloride or trimethylsilyl triflate.

The coupling can be carried out at any temperature that achieves the desired results, i.e., that is suitable for the reaction to proceed at an acceptable rate without promoting decomposition or excessive side products. Preferred temperatures are from −50° C. to 100° C.

Any reaction solvent can be selected that can achieve the necessary temperature and that can solubilize the reaction components. Nonlimiting examples are any aprotic solvent including, but not limiting to, alkyl solvents such as hexane and cyclohexane, toluene, THF, dioxane, acetonitrile, dichloromethane, dichloroethane, diethyl ether, pyridine, or any combination thereof, preferably dichloromethane.

Subsequently the nucleoside can be deprotected by methods well known to those skilled in the art, as taught in Greene, et al., *Protective Groups in Organic Synthesis*, John Wiley and Sons, Second Edition, 1991. For example, a t-butyldiphenylsilyl protected 5'—OH can be deprotected with a 1N TBAF solution of THF at room temperature. Alternatively, a 5'—OH protected with an acyl group can be deprotected, but not limited to, with ammonia or organic amine in an alcohol and water, such as ethanol and water.

Compounds of the present invention have at least two chiral centers, and may exist in and be isolated in optically active and racemic forms. Some compounds may exhibit polymorphism. The present invention encompasses racemic, optically-active, polymorphic, chiral, diastereomeric or stereoisomeric form, or mixtures thereof, of a compound of the invention, which possess the useful properties described herein. It will be appreciated that certain compounds of the present invention contain an asymmetrically substituted carbon atom, and may be isolated in optically active or racemic forms. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. All chiral, diastereomeric, racemic forms and all geometric isomeric forms of a structure are intended, unless the specific stereochemistry or isomer form is specifically indicated.

Optically active forms of the compounds can be prepared using any method known in the art, including by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatogaphy—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including simulated moving bed chromatography, is used in one embodiment. A wide variety of chiral stationary phases are commercially available.

The invention will be further understood by the following non-limiting Examples.

EXAMPLES

Melting points were determined on a Mel-temp II apparatus and are uncorrected. NMR spectra were recorded on a Varian 400 AMX spectrometer at 400 MHz for $^1$H NMR and 100 MHz for $^{13}$C NMR with TMS as internal standard. Chemical shifts (δ) are reported in parts per million (ppm), and signals are reported as s (singlet), d (doublet), t (triplet), q (quartet), m (multiplet), or bs (broad singlet). IR spectra were measured on a Nicolet 510P FT-IR spectrometer. Mass spectra were recorded on a Micromass Autospec high-resolution mass spectrometer. TLC were performed on Uniplates (silica gel) purchased from Analtech Co. Column chromatography was performed using either silica gel-60 (220–440 mesh) for flash chromatography or silica gel G (TLC grade, >440 mesh) for vacuum flash column chromatography. UV spectra were obtained on a Beckman DU 650 spectrophotometer. Elemental analysis was performed by Atlantic Microlab, Inc., Norcross, Ga., or Galbraith Laboratories, Inc., Knoxville, Tenn. HPLC was performed with a Waters HPLC system (Millipore Corporation, Milford, Mass.) equipped with a Model 600 controller, a Model 996 photodiode array detector and a Model 717 plus autosampler. Millennium 2010 software was used for system control, data acquisition and processing. A chiralyser polarimetric detector, Perkin-Elmer Model 241MC polarimeter (Wilton, Conn.), was used for the determination of optical rotations.

Example 1

1. Preparation of Ester (3).

A mixture of 1,2:5,6-O-diisopropylidene-D-mannitol (1, 13.1 g, 50 mmol) RuCl$_3$.H$_2$O (0.4 g), NaIO4 (0.2 mol, 42.8 g) and NaHCO$_3$ (0.11 mol, 9.24 g) in CCl$_4$ (60 mL), CH$_3$CN (60 mL) and H$_2$O (90 mL) was stirred at room temperature for 3 h. Organic layer was removed and the aqueous layer was concentrated to dryness under reduced pressure. The residue was refluxed in EtOH (300 mL) for 1 h and filtered. The filtrate was concentrated to dryness and co-evaporated with toluene (50 mL). The residue was mixed with bromoacetaldehyde diethyl acetal (50 mmol, 7.52 mL) in DMF (100 mL). The mixture was refluxed for 5 h. Solvent was removed under vaccum. The residue was treated with EtOAc (200 mL) and the mixture was washed with H$_2$O (50 mL×2). The organic layer was dried (Na$_2$SO$_4$). Solvent was removed to give compound 3 (13.5 g, 50%). $^1$H-NMR (CDCl3): $^1$H-NMR (CDCl3): δ 4.70 (t, 1H, CHOEt), 4.62 (m, 1H, 2-H), 4.18 (m, 4H, 2×CH$_2$), 3.50–3.75 (m, 4H, 2×MeCH$_2$), 1.50, 1.40 (ss, 6H, C(Me)$_2$), 1.20 (t, J=6.8 Hz, 6H, 2×CCH$_3$).

2. Preparation of Compound (5).

A solution of compound 3 (1.0 g, 4.2 mmol) in formic acid (80% in H$_2$O, 20 mL) was stirred at room temperature for 1 h and 20 min. The solution was concentrated to dryness at below 35° C. The residue was co-evaporated with toluene (2×10 mL) to give a crude diol as an oil which was dissolved in acetonitrile (50 mL, containing 0.01% of H$_2$O). To the solution was added BF$_3$.OEt$_2$ (8.4 mmol, 1.065 mL) and stirred at room temperature for 20 h. EtOAc (100 mL) was added and the resulting solution was washed with H$_2$O (10 mL) and aqueous NaHCO$_3$ (3×10 mL). The organic solution was dried (Na$_2$SO$_4$). Solvent was removed and the residue was purified by silica gel column (5% MeOH/CH$_2$Cl$_2$) to give compound 5 as solid. $^1$H-NMR (CDCl3): δ 5.26 (s, 1H, 2-H), 4.92 (d, J=12.4 Hz, 1H), 4.69 (dd, J=1.2, 6.8 Hz, 1H), 4.49 (dd, J=1.2, 8.8 Hz, 1H), 4.19 (d, J=12.8 Hz, 1H), 4.05 (dd, J=7.2, 9.2 Hz, 1H).

3. Preparation of 4-acetoxydioxolane (7).

Compound 5 (200 mg, 1.5 mmol) was dissolved in THF (20 mL). To the solution was added 1N NaOH (2 mL, 2 mmol) and the mixture stirred at room temperature for 2 h. To the mixture was added NaHCO$_3$ (3 mmol, 252 mg) then excess BzCl (1.5 mL) and the mixture was stirred at room temperature for 2 h. EtOAc (50 mL) was added and the pH of the solution was adjusted to 1.5 by addition of 6N HCl. Organic solution was washed with H$_2$O (2×5 mL) and dried (Na$_2$SO$_4$). Solvent was removed and the residue was dissolved in THF (20 mL). To the solution was added pyridine (1.5 mmol, 118 mg) and Pd(OAc)$_4$ (3 mmol, 1.33 g) and the mixture was stirred at room temperature for 16 h. EtOAc (100 mL) was added and the mixture was washed with H$_2$O (3×20 mL). The organic layer was dried (Na$_2$SO$_4$). Solvent was removed and the residue was purified by silica gel column (10% EtOAc/Hexanes) to give compound 7 (38%). $^1$H-NMR (CDCl$_3$): δ 8.10–7.42 (m, 5H, Bz), 6.44, 6.38 (ddd, J=2.0, 4,4, 4.0 Hz, 1H, 4-H), 5.55, 5.46 (tt, J=3.2, 4.0 Hz, 1H, 2-H), 4.43 (m, 2H, 2-CH$_2$), 4.24 (m, 1H, 5-H), 4.02 m, 1H, 5'-H), 2.11, 1.99 (ss, 3H, Ac).

4. Preparation of 2'-hydroxymethyl-1'3'-dioxolan-yl-2-amino-6-para-methoxybezenemercaptopurine (9).

A suspension of 2-amino-6-chloropurine (2 mmol, 339 mg) and (NH$_4$)$_2$SO$_4$ (10 mg) in HMDS (10 mL) was refluxed for 5 h and the clear solution was evaporated to dryness. The residue was dissolved in CH$_2$Cl$_2$ (10 mL). To the solution was added a solution of the acetate 7 in (133 mg, 0.5 mmol) in CH$_2$Cl$_2$ (5 mL) and iodotrimethylsilane (TMSI, 2.6 mmol, 0.37 mL) at 0° C. The mixture was stirred at room temperature for 20 h and refluxed for 3 h. The resulting mixture was cooled to room temperature and neutralized to pH7. Organic solution was dried (Na$_2$SO$_4$) and the solvent was removed. The residue was purified by silica gel column (5% MeOH/CH$_2$Cl$_2$) to give product as a mixture of α/β-isomer, 2'-benzoyloxymethyl-1',3'-dioxolan- 4'-yl-2-amino-6-chloropurine (132 mg, 70%) with a ratio of 3/2 in favor of β-isomer.

A mixture of p-methoxybenzenethiol (0.14 mL, 1 mmol) and NaH (48 mg, 2 mmol) in DMF (5 mL) was stirred at room temperature for 10 min. To the mixture was added a solution of the protected nucleosides in in DMF (2 mL) and the mixture was stirred at room temperature for 20 h. Solvent was removed and the residue was dissolved in MeOH (20 mL) and butylamine (2 mL) was added. The solution was refluxed for 20 h. Solvent was removed and the residue was purified by silica gel column to give final nucleoside, 2'-hydroxymethyl-1'3'-dioxolan-yl-2-amino-6-para-methoxybezenemercaptopurine (9). NMR (CDCl$_3$): δ 7.91 (s, 1H, 8-H), 7.50 (d, J=8.4 Hz, 2H, Ph), 6.95 (d, J=8.4 Hz, 2H, Ph), 6.24 (dd, J=2.8, 8.4 Hz, 1H, 4'-H), 5.25 (t, J=2.4 Hz, 1H, 2'-H), 4.86 (brs, 2H, NH$_2$), 4.47, 4.30 (mm, 2H, 5'-H), 3.91 (d, J=1.2 Hz, 2H, 6'-H), 3.85 (s, 3H, OCH$_3$).

Modifications and preferred adjustments of the present invention described herein will be obvious to those of skill in the art. All of these modifications and adjustments are considered within the scope of the present invention.

We claim:

1. A process for preparing a D- or L-dioxolane nucleoside of formulae III–VI:

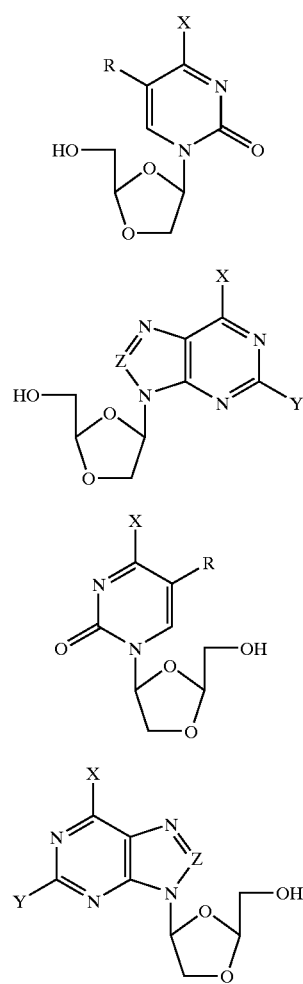

wherein
R is H, halogen, OH, OR', SH, SR', NH$_2$, NHR', NR'$_2$, lower alkyl of C$_1$–C$_4$, CH=CH$_2$, N$_3$C=CH$_2$, CO$_2$H, CO$_2$R', CONH$_2$, CN, CONHR', CH$_2$OH, CH$_2$CN, CH$_2$CH$_2$OH, CF$_3$, CH$_2$CH$_2$F, CH=CHCO$_2$H, CH=CHCO$_2$R', CH=CHCl, CH=CHBr, or CH=CHI;

R' is lower alkyl (C$_1$–C$_4$);

each X and Y is independently H, halogen, OH, OCH$_3$, SH, SCH$_3$, NH$_2$, NHR', NR'$_2$, or CH$_3$; and Z is CH, or C—X;

comprising the steps of:
1) preparing compounds of formula VII or VIII:

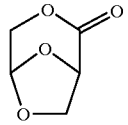

VII

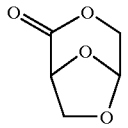

VIII by:
a) oxidation of 1,2-O-protected-glycerol to an acid salt, or hydrolysis of methyl (R)- or (S)-1,2-O-protected-glycerate to form intermediate 1:
b) alkylation of intermediate 1 with a compound of formula X'CH$_2$CH(OR$_6$)$_2$, wherein X' is halogen or pseudohalogen, and R$_6$ is alkyl or aralkyl (C$_{1-20}$);
c) cyclization with an acid catalyst optionally with hydrolysis of the acetal;
2) hydrolyzing the ester group of the compound of formula VII or VIII followed by protection of the resulting alcohol under basic conditions to form a compound of formula 6 (including D- and L-isomers):

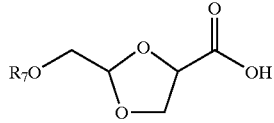

6 wherein R$_7$ is a protecting group;
3) decarboxylating the carboxylic group of compound 6; and
4) coupling with a purine or pyrimidine base or its derivative, followed by deprotection to form a D- and L-dioxolane nucleoside of formulae III–VI.

2. The process according to claim 1, wherein the basic conditions used for hydrolysis of the ester of formula VII and VIII in step 2 include a base that is an organic or inorganic base or combination thereof.

3. The process of claim 2 wherein the base is an aqueous alkali or alkali earth metal base.

4. The process of claim 3, wherein the base is aqueous NaOH or aqueous KOH.

5. The process of claim 1, wherein the oxidation in step 1 is conducted using an oxidizing agent selected from the group consisting of NaIO$_4$/RuCl$_3$ hydrate, NaOCl/RuCl$_3$ hydrate, KMnO$_4$, NaIO$_4$ and KIO$_4$ and combinations thereof.

6. The process of claim 1, wherein decarboxylation in step 3 is carded out at from about −10° C. to 100° C., in an aprotic solvent or water, or combination thereof.

7. The process of claim 6, wherein the solvent is an aprotic solvent.

8. The process of claim 7, wherein the solvent is hexane, cyclohexane, toluene, ethyl acetate, THF, dioxane, acetonitrile, dichloromethane, dichloroethane, diethyl ether, dimethylformamide (DMF), dimethylsulfoxide (DMSO), dimethylacetamide, or a combination thereof.

9. The process of claim 1, wherein the acid catalyst in step 1 is a Lewis acid.

10. The process of claim 1, wherein the acid catalyst in step 1 is $BF_3$ etherate.

11. The process of claim 1, comprising coupling the purine or pyrimidine base or its derivative by:
   silylation of the purine or pyrimidine base or its derivative; and
   coupling of the silylated purine or pyrimidine base or its derivative to the compound of Formula 6 in the presence of a Lewis acid.

12. The process of claim 11, wherein the Lewis acid is selected from the group consisting of tin tetrachloride, titanium tetrachloride or trimethylsilyl triflate.

13. The process of claim 11, wherein the purine or pyrimidine base or its derivative is silylated with hexamethyldisilazane (HMDS).

14. The process of claim 1, further comprising isolating the nucleoside of formula II–VI in optically active form.

15. The process of claim 14, wherein the optically active form is isolated by resolution of a racemic form by recrystallization techniques, by synthesis from optically-active starting materials, by chiral synthesis, or by chromatographic separation using a chiral stationary phase.

16. The process of claim 1, wherein the purine or pyrimidine base is selected from the group consisting of adenine, $N^6$-alkyl-purines, $N^6$-acylpurines (wherein acyl is C(O) (alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluoro-cytosine, 5-methylcytosine, 6-azapyrimidine, including 6-aza-cytosine, 2- and/or 4-mercapto-pyrimidine, uracil, 5-halouracil, including 5-fluorouracil, $C^5$-alkylpyrimidines, $C^5$-benzyl-pyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amido-pyrimidine, $C^5$-cyanopyrimidine, $C^5$-nitropyrimidine, $C^5$-aminopyrimidine, $N^2$-alkyl-purines, $N^2$-alkyl-6-thiopurines, 5-azacytidinyl, 5-aza-uracilyl, triazolopyridinyl, imidazolo-pyridinyl, pyrrolopyrimidinyl, and pyrazolopyrimidinyl.

17. The process of claim 1, wherein $R_7$ is acyl, silyl, alkyl or an aralkyl group ($C^{1-20}$).

* * * * *

UNITED STATES PATENT AND TRADEMARK OFFICE
CERTIFICATE OF CORRECTION

PATENT NO.     : 6,855,821 B2
DATED          : February 15, 2005
INVENTOR(S)    : Jinfa Du and Kyoichi A. Watanabe It is certified that error appears in the above-identified patent and that said Letters Patent is hereby corrected as shown below:

Column 24,
Lines 18-23, to the right of the structure for formula VIII, insert a semicolon.
Line 28, "1:" should read -- 1; --.
Line 66, "is carded out" should read -- is carried out --.

Column 26,
Line 25, "$(C^{1-20})$" should read -- $(C_{1-20})$ --.

Signed and Sealed this

Sixth Day of September, 2005

JON W. DUDAS
*Director of the United States Patent and Trademark Office*